US009085535B2

(12) United States Patent
Heindl et al.

(10) Patent No.: US 9,085,535 B2
(45) Date of Patent: Jul. 21, 2015

(54) METHOD AND SUBSTANCES FOR THE PREPARATION OF N-SUBSTITUTED PYRIDINIUM COMPOUNDS

(75) Inventors: Dieter Heindl, Paehl (DE); Peter Gebauer, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/359,661

(22) Filed: Jan. 27, 2012

(65) Prior Publication Data

US 2012/0190855 A1 Jul. 26, 2012

Related U.S. Application Data

(63) Continuation of application No. PCT/EP2010/004524, filed on Jul. 23, 2010.

(30) Foreign Application Priority Data

Jul. 27, 2009 (EP) .................................... 09166456

(51) Int. Cl.
*C07D 213/803* (2006.01)
*C07D 213/80* (2006.01)

(52) U.S. Cl.
CPC .......... *C07D 213/803* (2013.01); *C07D 213/80* (2013.01)

(58) Field of Classification Search
CPC .......................... C07D 213/80; C07D 213/803
See application file for complete search history.

(56) References Cited

U.S. PATENT DOCUMENTS

| | | | |
|---|---|---|---|
| 4,411,995 A | | 10/1983 | Whitesides et al. |
| 4,668,354 A | * | 5/1987 | Levy .............................. 205/688 |
| 2008/0213809 A1 | | 9/2008 | Heindl et al. |

FOREIGN PATENT DOCUMENTS

| | | | |
|---|---|---|---|
| CA | 2614792 | * | 2/2007 |
| DE | 3328808 A1 | | 2/1985 |
| WO | 2007/012494 A1 | | 2/2007 |

OTHER PUBLICATIONS

Benoiton, N. L. in Houben-Weyl Methods in Organic Chemistry, vol. E22,—Synthesis of Peptides and Peptidomimetics, vols. 1-5 (Workbench Edition), Chapter 3.2 "Active Esters", 2004, pp. 443-474, Online "http://www.thieme-chemistry.com/fileadmin/Thieme/HW 100/pdf/april/Benoiton_ZAT.pdf" accessed Jul. 1, 2013.*
Matsumoto, K., Hashimoto, S., "Direct aminolysis of nonactivated and thermally unstable esters at high pressure." Chem. Ber., 122: 1357.*
International Search Report issued Jun. 22, 2011 in PCT Application No. PCT/EP2010/004524, 5 pages.
Arnold, Z. and Holý, A., "The Preparation of Substituted Pentamethinium Salts," Collection of Czechoslovak Chemical Communications, 1965, pp. 40-46, vol. 30.
Cheng, Wei-Chieh and Kurth, Mark J., "The Zincke Reaction. A Review," Organic Preparations and Procedures International, 2002, pp. 585-608, vol. 34, No. 6.
Eda, Masahiro et al., "The Solid-Phase Zincke Reaction: Preparations of ω-Hydroxy Pyridinium Salts in the Search for CFTR Activation," Journal of Organic Chemistry, 2000, pp. 5131-5135, No. 65.
Goulioukina, Natasha et al., "Synthesis of Nicotinamide Adenine Dinucleotide (NAD) Analogues with a Suger Modified Nicotinamide Moiety," Helvetica Chimica Acta, 2007, pp. 1266-1278, vol. 90.
Greene, Theodora W. and Wuts, Peter G.M., "Protective Groups in Organic Synthesis Third Edition," 1999, pp. 308-322, 725-727, John Wiley & Sons, Inc.
Kam, Bernard L. and Oppenheimer, Norman J., "Synthesis of a new class of D-aldopentofuranosylamines, the 5-O-trityl-D-aldopentofuranosylamines," Carbohydrate Research, 1979, pp. 275-280, vol. 77.
Kam, Bernard L. et al., "Pyridine Coenzyme Analogues. Synthesis and Characterization of α- and β-Nicotinamide Arabinoside Adenine Dinucleotides," Biochemistry, 1987, pp. 3453-3461, vol. 26.
Sicsic, Sames et al., "Activity of NMN+, nicotinamide ribose and analoges in alcohol oxidation promoted by horse-liver alcohol dehydrogenase, Improvement of this activity and structural requirements of the pyridine nucleotide part of the NAD+ coenzyme," European Journal of Biochemistry, 1986, pp. 403-407, vol. 155.
Vianna, Gustavo H. R. et al., "Rapid Microwave-Promoted Solvent-Free Synthesis of Zincke's Salts and their Conversion into Chiral Pyridinium Salts in Water," Letters in Organic Chemistry, 2008, pp. 396-398, vol. 5.
Wypych, Jean-Charles et al., "Reaction of Aldimine Anions with Vinamidinium Chloride: Three-Component Access to 3-Alkylpyridines and 3-Alkylpyridinium Salts and Access to 2-Alkyl Glutaconaldehyde Derivatives," Journal of Organic Chemistry, 2008, pp. 1169-1172, vol. 73.
Yang, Tianle et al., "Synthesis of Nicotinamide Riboside and Derivatives: Effective Agents for Increasing Nicotinamide Adenine Dinucleotide Concentrations in Mammalian Cells," Journal of Medicinal Chemistry, 2007, pp. 6458-6461, vol. 50.

(Continued)

*Primary Examiner* — David K O Dell
(74) *Attorney, Agent, or Firm* — Stinson Leonard Street LLP

(57) ABSTRACT

Methods for the synthesis of N-substituted carboxylated pyridinium compounds by reaction of a pentamethine precursor with a primary amine are provided. In this reaction an N-substituted alkoxycarbonyl pyridinium heterocycle is formed.

10 Claims, No Drawings

(56) References Cited

OTHER PUBLICATIONS

English Translation of Example 1 of DE 3328808 A1, published on Feb. 21, 1985, Applicant BYK Gulden Lomberg Chem Fab.

Sanchez-Salvatori, Maria del Rayo et al., "3-Substituted pentadienals derivatives from condensation of imines anions to malonaldehyde equivalents. A C-C-C + C-C + N type entry to 3-alkyl substituted pyridinium salts," Tetrahedron Letters, 2006, pp. 5503-5506, vol. 47.

* cited by examiner

METHOD AND SUBSTANCES FOR THE PREPARATION OF N-SUBSTITUTED PYRIDINIUM COMPOUNDS

RELATED APPLICATIONS

This application is a continuation of International Application No. PCT/EP2010/004524, filed Jul. 23, 2010, which claims the benefit of European Patent Application No. 09166456.5, filed Jul. 27, 2009, the disclosures of which are hereby incorporated by this reference in their entirety.

BACKGROUND

1. Technical Field

The present disclosure relates to a method for the synthesis of N-substituted carboxylated pyridinium compounds.

2. Description of the Related Art Pyridinium compounds are of interest in, for example, drug design and as general intermediates for organic syntheses, such as in natural product synthesis. Certain substituted pyridinium compounds are useful in the synthesis of NAD or NAD analogs, respectively. Additionally, certain heteroaryl substituted pyridinium compounds have been studied in relation to solvatochromism.

Currently, the standard method for the synthetic production of substituted pyridinium compounds includes alkylation of pyridine derivatives. However, this reaction is only convenient when using primary alkyl halides. When secondary or tertiary alkyl halides are used, elimination occurs as an unwanted side reaction and yields are generally low. Moreover, when the alkylation is performed with alkyl halides having a halogen atom attached to an asymmetric carbon atom, racemization may occur during the nucleophilic displacement reaction.

Zincke salts may be prepared by reacting a pyridinium compound with 2,4 dinitro halobenzol preferably with 2,4 dinitrochlorbenzol and 2,4 dinitrobrombenzol.

As is apparent from the above description, the activation reagents presently used in production of substituted pyridinium compounds are toxic, explosive, and/or otherwise hazardous and are therefore limited to small scale research applications. Additionally, while there have been sporadic attempts at performing Zincke reactions in an ecofriendly manner, for example by using microwave assisted synthesis, such attempts still rely on explosive dinitrophenyl compounds and are not capable of being scaled up without taking expensive precautionary measures.

It is also known that various 2-alkylaminopentadienimin derivatives react with NH4OAc or primary amines (R—NH2) under acidic conditions to form the corresponding 3-alkylated pyridines, respectively, 1-R-3-alkyl-substituted pyridinium compounds. The required 2-alkylaminopentadienimin compounds are accessible from N-tertbutylimino derivatives of aldehydes, deprotonated with LDA and reacted with vinamidinium chloride.

However, the utility of this method is severely limited. Reactive groups, such as ester functions, may not be introduced in position 2 of the aminopentadienimin system, which, for example, would be a prerequisite for the synthesis of nicotinic acid ester derivatives.

As such, there is a need for a new and improved method of synthesis of N-substituted pyridium compounds which avoids hazardous activation reagents and which overcomes other problems known in the art.

SUMMARY

The present disclosure relates to methods of synthesizing N-substituted pyridinium compounds with novel, less hazardous activation reagents allowing for safer production procedures and for easier, less risky, and more efficient production of such compounds at much larger scales.

According to embodiments of the instant disclosure, methods for synthesis of N-substituted carboxylated pyridinium compounds by reacting a pentamethine precursor with a primary amine, are provided. According to such embodiments, N-substituted carboxylated pyridinium heterocycle is formed.

Embodiments of the present disclosure relate to a method for the synthesis of an N-substituted pyridinium-3 carboxylic ester. According to some embodiments these methods comprise the steps of: providing a pentamethinium salt and reacting the pentamethinium salt with a primary amine, thereby obtaining an N-substituted pyridinium-3-carboxylic acid ester. The N-substituted pyridinium-3-carboxylic acid ester may thereafter be recovered.

As described in further detail herein, the limitations of prior methods of synthetic production of substituted pyridinium compounds, such as described above, may be overcome by using the Zincke reaction of the instant disclosure. According to some embodiments, the Zincke reaction includes the reaction of Zincke salts with alkyl or aryl amines. Zincke salts comprise activated pyridinium salts capable of reacting with a primary amine (R—NH2). According to specific embodiments, ring opening is induced at the nitrogen in 2 or 6 position, respectively, which in turn is followed by ring closing (of the former ring) to produce an R-substituted pyridinium compound. Embodiments of the instant disclosure may also be performed with hydrazines, hydroxyl amine, and carboxylic acid hydrazides. Embodiments of the "Zincke reactions" disclosed herein may, for example, be used for in-solution and for solid phase organic syntheses.

Additionally, the present disclosure also provides the surprising findings that the pentamethinium salt 5-dimethylamino-4-methoxycarbonyl-penta-2,4-dimethyl-dienylidene ammoniumtetrafluoroborate cyclisizes with different primary amines (R—NH2) in one step to form the corresponding 1-R-substituted nicotinic acid methyl esters. As disclosed herein, using this method, it is possible to obtain nicotinamide "carbaribosid", (3-Carbamoyl-1-((1R,2S,3R,4R)-2,3-dihydroxy-4-hydroxymethyl-cyclopentyl)-pyridinium; chloride), a precursor in the synthesis of a carba analog of NAD.

According to an embodiment of the present disclosure, a method for the formation of N-substituted pyrimidinium derivatives is provided. According to specific embodiments, an aminopentadieniminium compound is provided. A subsequent reaction of the aminopentadieniminium compound with a primary amine (R6-NH2) leads to a corresponding 1-R6-substituted pyridinium compound. The methods disclosed herein avoid the above-mentioned problematic activation reagents. Moreover the formation of the N-substituted pyrimidinium derivatives is almost quantitative and can be scaled up easily.

Based on the unexpected findings presented herein, many of the problems known from the art can be avoided and overcome.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

An embodiment the present disclosure relates to a method for synthesis of an N-substituted pyridinium-3-carboxylic acid ester comprising the steps of: providing a pentamethinium salt; reacting the pentamethinium salt (of the providing step) with a primary amine; and obtaining an N-substituted pyridinium-3-carboxylic acid ester.

According to one embodiment the present disclosure relates to a method for synthesis of an N-substituted carboxylated pyridinium compound comprising the steps of:

(a) providing a pentamethinium salt according to Formula I.

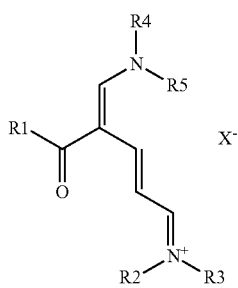

Formula I wherein X⁻ is a counter ion;
R1 is alkoxy selected from O-methyl, O-ethyl, O-propyl, and O-isobutyl; and
R2 to R5 independently are methyl or ethyl,
b) reacting the pentamethinium salt of step (a) with a primary amine of Formula II,

Formula II wherein R6 is linear, branched, or cyclic, optionally substituted alkyl, and
c) thereby obtaining/recovering an N-substituted pyridinium compound of Formula III

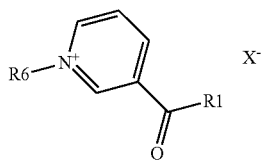

Formula III wherein X—, R1, and R6 are as defined above.

Examples of suitable counter ions include dodecyl sulfate, chloride, hexafluorophosphate (PF6⁻), tetrafluoroborate (BF4⁻), and perchlorate (ClO4⁻). According to more specific embodiments the counter ion is dodecyl sulfate, tetrafluorophosphate (POF4⁻) or tetrafluoroborate.

As defined above, R6 may be linear, branched, or cyclic optionally-substituted alkyl. In one embodiment the alkyl is a linear C1-C6 alkyl, or a branched C3-C6 alkyl, or a cyclic C5-C6 alkyl, or the substituted alkyl is a substituted linear C1-C6 alkyl, or a substituted branched C3-C6 alkyl, or a substituted cyclic C5-C6 alkyl. According to some embodiments, R6 is a furanosyl or a cyclopentyl residue. According to specific embodiments the compound according to Formula II is a linear or branched alkyl amine or is a furanosylamine or a cyclopentylamine.

It has surprisingly been found that the synthesis according to the present disclosure has very high yields of the desired product if such synthesis is performed under reaction conditions wherein both the primary amine, as well as the primary amine in protonated form, are present. The present disclosure thus provides methods for the synthesis of an N-substituted pyridinium-3 carboxylic ester comprising the steps of (a) providing a pentamethinium salt (b) reacting the pentamethinium salt of step (a) with a primary amine in the presence of the primary amine in protonated form, and (c) thereby obtaining/recovering the N-substituted pyridinium-3-carboxylic acid ester.

Methods according to the present disclosure may be performed under reaction conditions wherein the ratio of the primary amine to its corresponding protonated amine is from 2:1 to 1:50. According to specific methods, the ratio of primary amine to its corresponding protonated amine is from 1:1 to 1:20. In other specific embodiments the ratio of primary amine to its corresponding protonated amine is from 1:2 to 1:15.

The presently disclosed methods are appropriate to produce alkoxycarbonyl pyridinium compound. In one embodiment the present disclosure relates to the use of a pentamethinium salt in a method wherein R1 is OCH3, i.e. to the production of an N-substituted methoxycarbonyl pyridinium compound.

In a further specific embodiment the present disclosure relates to the use of a pentamethinium salt in a method wherein R2 to R5 each are methyl.

One focus of the investigations set forth in the following Examples section is on the conversion of the pentamethinium salt 5-dimethyl-amino-4-methoxycarbonyl-penta-2,4-dimethyl-dienylidene ammoniumtetrafluoroborate with amino carbaribose ((1R,2S,3R,4R)-2,3-dihydroxy-4-hydroxymethyl)-1-aminocyclopentan). It has been found that amino carbaribose reacts almost quantitatively with the pentamethinium salt, e.g. in the presence of pyridiniumtetrafluoroborate as a counter ion, to obtain the N-substituted nicotinic acid ester derivative. Surprisingly the ester function was not affected by the primary amine.

Side reactions, such as the formation of the dimethylamide due to the attack of released dimethylamine on the ester function of the formed methylnicotinate, can be eliminated almost completely by using an appropriate mixture of amino carbaribose and the corresponding hydrochloride. It is convenient to slowly and continuously add the pentamethinium salt mixed with an equimolar amount methanesulfonic acid.

The present method can, however, be extended to other primary amines. As the skilled artisan appreciates, such primary amines can comprise further substituents which do not interfere with the cyclization reaction. In a specific embodiment the compound R6-NH2 is a substituted primary alkyl amine.

Specific substituted primary alkyl amines suitable for use in a method according to the present disclosure are pure stereoisomers of amino alcohols and amino acids.

In some embodiments, an amino alcohol is derived from any naturally occurring or any commercially available non-natural amino acid. In very specific embodiments the amino alcohol is selected from the group consisting of serinol, threoninol, phenylalaminol, 2,5-diamino-1-pentanol (from ornithin) and 2,6-diamino-1-hexanol (from lysine).

Where the compound according to Formula II is an amino acid, the amino acid may be selected from any naturally occurring or any non-natural amino acid. In a specific embodiment the amino acid either is a naturally occurring amino acid or a non-naturally occurring amino acid, including commercially available amino acids. In specific embodiments the compound according to Formula II is an amino acid selected from serine threonine, phenylalanine, ornithin, lysine, and leucine.

According to an alternative embodiment, di- or polyamines without protected amino groups can be reacted with two or more equivalents of the pentmethinuim salt in order to form di-pyridinium or poly-pyridinium compounds.

Other specific primary amines include amines substituted with furanosyl sugar moieties or analogs of such furanosyl sugar moieties, which optionally are phosphorylated at an OH group or compromise protected hydroxyl groups, whereas the protecting groups are benzyl, acetal, silyl and trityl or compromise F or methoxy groups instead of OH groups. In very specific embodiments, a furanosyl sugar or such analogs which are suitable for the synthesis of NAD or Nicotinamidmononucleosid, and analogs thereof, are used.

The use of furanosylamines for the synthesis of NAD or Nicotinamidmononucleoside and analogs thereto is described in detail in the following references: Kam, B. L. et al., Biochemistry 26 (1987) 3453-3461; Sicsic, S. et al., European Journal of Biochemistry 155 (1986) 403-407; Kam, B. L. and Oppenheimer, N. J., Carbohydrate Research 77 (1979) 275-280; and U.S. Pat. No. 4,411,995, the entire disclosures of which are incorporated herein by this reference.

Specific suitable furanosylamines are the beta- and alpha-anomers of D- and L-ribose, xylose and arabinose.

Other specific embodiments include cyclopentylamines, which are the carba analogues of furanosylamines like Beta-D-ribofuranosyl amine, 2 deoxyribofuranosylamine, or 2,3 dideoxy ribosylfuranosylamine i.e. (1R,2S,3R,4R)-2,3 Dihydroxy-4-hydroxymethyl-1-aminocyclopentane, (1S,3R,4R)-3-Amino-4-hydroxy-cyclo-pentanemethanol, or (1R-cis)-3-amino-Cyclopentane-methanol.

In a further specific method according to the present disclosure, a pentamethinium salt is reacted with a primary amine, wherein the primary amine is (1R, 2S, 3R, 4R)-2,3 Dihydroxy-4-hydroxymethyl-1-aminocyclopentane. Reacting 5-dimethyl-amino-4-methoxycarbonyl-penta-2,4-dimethyl-dienylidene ammoniumtetrafluoroborate with this primary amine leads to the formation of nicotinamido-carba riboside (3-Methoxycarbonyl-1-((1R,2S,3R,4R)-2,3-dihydroxy-4-hydroxymethyl-cyclopentyl)-pyridinium chloride), which is easily converted with ammonia in Nicotinamido-carba riboside (3-Carbamoyl-1-((1R,2S,3R,4R)-2,3-dihydroxy-4-hydroxymethyl-cyclopentyl)-pyridinium tetrafluoroborate. Nicotinamido-carba ribosid is a compound which is a key to the synthesis of the carba analog to NAD. Carba-NAD and its uses are described in detail in WO 2007/012494, the entire disclosure of which is incorporated herein by this reference.

Other specific substituted primary amines are selected from 3-Amino tetrahydrofuranes or protected 3-Amino-pyrrollidines, e.g. (2R,4R)-4-Aminotetrahydrofuran-2-methanol (a heterocyclic analog of 2,3-dideoxyribosylamine) cyclohexylamines and Cyclohex-2-enyl amines, e.g. 6 ring sugar analogs as disclosed by Goulioukina, N. et al., Helvetica Chimica Acta 90 (2007) 1266-1278.

Suitable examples of phosphorylated amino sugars include (1R,4S,6S)-4-Amino-6-hydroxy-2-cyclohexene-1-methanol-1-(dihydrogen phosphate), 2-Amino-1,5-anhydro-2-deoxy-6-(dihydrogen phosphate) D-Altritol, 2-Amino-1,5-anhydro-2,3-dideoxy, and 6-(dihydrogen phosphate) D-arabino-Hexitol.

As the skilled artisan will appreciate even primary amines having an additional principally nucleophilic substituent can be used. In this case, the further nucleophilic group has to be protected by an appropriate protecting group. Protecting groups are well known from the art and reviewed in standard text books (e.g. Greene, T. W., Protective groups in organic synthesis, John Wiley&Sons, Inc. (1981) New York, Chichester, Brisbane, Toronto). Amino groups may be protected by boc-, phthaloyl- or trifluoracetyl-protecting groups, and mercapto groups are protected as disulfide.

According to another specific embodiment, the present method is used in combination with other primary amines such as an amino-modified TAMRA dye. By cyclization of the pentamethinium salt with a mixture of 5-(and 6)-((N-(5-aminopentyl)amino) carbonyl)-tetramethyl rhodamine, under conditions comparable to the reaction with amino carbaribose, the corresponding N-substituted methylnicotinate can be obtained in a good yield.

The reactivity of the obtained 3-methoxycarbonyl pyridinium system opens new opportunities for the use of the described cyclization. In a specific embodiment the N-substituted methyl or ethyl nicotinates formed in a method according to the present disclosure are used as alternative linkers for coupling procedures, such as for coupling of biomolecules including coupling of oligonucleotides to an effector group, a hapten, a fluorescent or a luminescent compound. The present disclosure thus also relates to conjugates comprising an N-substituted methyl or ethyl nicotinate as a linker.

The following examples are provided to illustrate specific embodiments of the present disclosure, the true scope of which is set forth in the appended claims. It is understood that modifications can be made in the procedures set forth without departing from the spirit of the disclosure.

The following examples, set forth below, are provided for the purpose of demonstrating various embodiments of the instant disclosure and aiding in an understanding of the present disclosure. These examples are not intended to, and should not be understood as, limiting the scope or spirit of the instant disclosure in any way.

EXAMPLES

Example 1

Synthesis of 5-Dimethylamino-4-methoxycarbonyl-penta-2,4-dienylidene-dimethyl-ammoniumtetrafluoroborate Example 1.1

Synthesis of Methyl-(2E)-3-(3-dimethylamino)prop-2-enoate

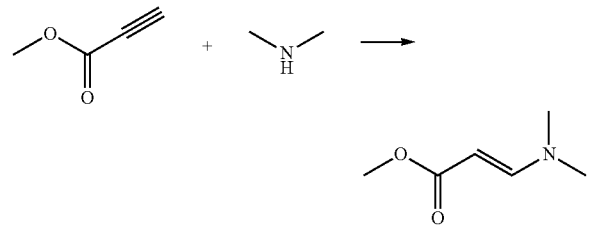

To a solution of methylpropiolate (68.0 ml, 0.764 mol) in 700 ml of dry THF a 2 M solution of N,N-dimethylamine in the same solvent (392 ml, 0.783 mol) was added within 1 h at room temperature. After removing the solvent the residue was dried for 1 h (37° C., 10-20 mbar) at the evaporator, resulting in a pale yellow solid. The crushed solid was washed with n-hexane to yield 93.0 g (94%) methyl-(2E)-3-(3-dimethylamino)prop-2-enoate that was pure according to TLC and 1H NMR.

Example 1.2

Synthesis of Pyridiniumtetrafluoroborate

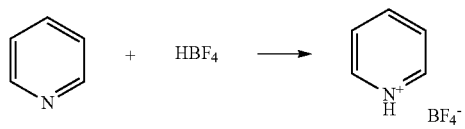

Tetrafluoroboric acid (250 ml, 2.00 mol) was added to cool (0° C.) pyridine (157.7 ml, 1.95 mol) and within 25 min a colorless precipitate was obtained. After the acid was completely added the mixture was further stirred for 30 min at the same temperature. Then the reaction mixture was filtered. The residue was washed twice with cold ethanol and dried 12 h at high vacuum to yield 201.9 g (60%) pyridiniumtetrafluoroborate as colorless crystals.

Example 1.3

Synthesis of 5-Dimethylamino-4-methoxycarbonyl-penta-2,4-dienylidene-dimethyl-ammoniumtetrafluoroborate

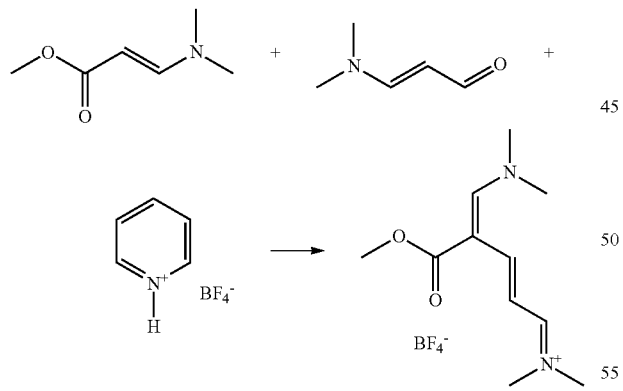

Pyridiniumtetrafluoroborate (283.7 g, 1.70 mol) was added to a solution of methyl-(2E)-3-(3-dimethylamino)prop-2-enoate in 442.5 ml acetic anhydride/acetic acid (2:1). The resulting suspension was cooled to 0° C. and 3-dimethylaminoacroleine (169.9 ml, 1.70 mol) was added slowly (3 h) while vigorously stirring and cooling with an ice bath to yield a yellow-brown precipitate. After further stirring for 2 h at room temperature the reaction mixture was filtered. The remaining solid was washed with diethylether several times and dried under reduced pressure. Recrystallization from i-propanol/ethanol (2:1) gave 326.7 g (65%) of the pentamethinium salt as yellow crystals.

Example 2

Synthesis of 3-Amino-5-hydroxymethyl-cyclopentane-1, 2-diol

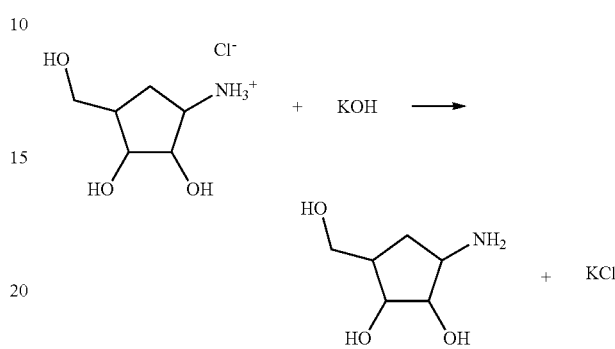

A 1M solution of KOH in EtOH (54.5 ml, 54.5 mmol) was added to a cooled (0° C.) solution of the hydrochloride (10.0 g, 54.5 mmol) solved in 540 ml EtOH. After 15 min stirring at room temperature the formed colorless precipitate was removed by filtration. The filtrate was concentrated under reduced pressure. The remaining oil was dried at the evaporator (1 h, 40° C.) yielding 9.01 g (112%) of amino carbaribose as a pale yellow oil. The obtained product is used for the following steps without further purification.

Example 3

Synthesis of 1-(2, 3-Dihydroxy-4-hydroxymethyl-cyclopentyl)-3-methoxycarbonyl-pyridinium-methansulfonate

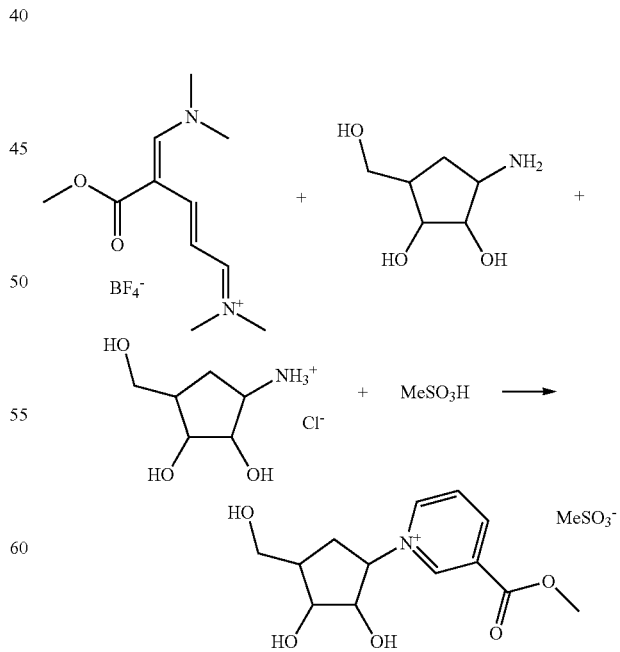

Vinamidinium salt (298.1 g, 1.00 mol) was solved in 1500 ml DMF and 1 equivalent of methanesulfonic acid (65.02 ml, 1.00 mol) was added. This mixture was dropped continuously and very slowly (within 5 h) into a refluxing solution (90° C.) of 3-Amino-5-hydroxymethyl-cyclopentane-1,2-diol (165.3 g, 0.90 mol) and 3-Amino-5-hydroxymethyl-cyclopentane-1,2-diol (25.8 g, 0.15 mol) in 1250 ml MeOH. After the complete addition of the vinamidinium salt solution the reaction mixture was cooled down to room temperature and 0.15 equivalents methanesulfonic acid were again added. The mixture was stirred for 12 h at the same temperature. After removing the solvent under reduced pressure, red-brown oil was obtained, which was further dried for 3 h (45° C., 4 mbar). Yield: 693.0 g (191%, containing salts and a larger amount of solvent).

Example 4

3-Carbamoyl-1-(2,3-dihydroxy-4-hydroxymethyl-cyclopentyl)-pyridinium-methansulfonate The crude 1-(2,3-Dihydroxy-4-hydroxymethyl-cyclopentyl)-3-methoxycarbonyl-pyridinium-methansulfonate material from Example 3 was rapidly converted into the corresponding amide without further purification.

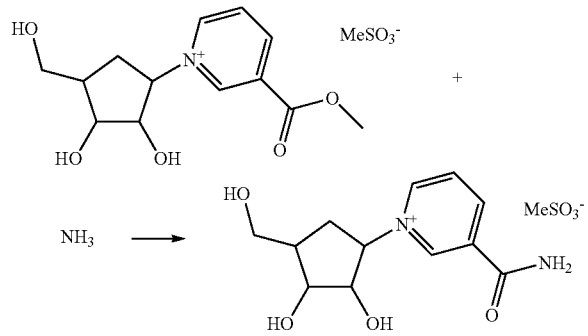

Crude 1-(2,3-Dihydroxy-4-hydroxymethyl-cyclopentyl)-3-methoxycarbonyl-pyridinium-methansulfonate 118.3 g, 173.7 mmol) was dissolved in 100.0 ml methanol. After the addition of methanolic ammonia (7M, 350.0 ml, 2.45 mol) the reaction mixture was stirred for 2.5 h. After removing the solvent under reduced pressure a red-brown oil was obtained that was further dried for 3 h (40° C., 10 mbar). This crude product is pre-purified with activated charcoal and used directly for the synthesis of cNAD (WO 2007/012494).

Example 5

Synthesis of 3-N,N-Dimethylcarbamoyl-1-(2,3-dihydroxy-4-hydroxymethyl-cyclopentyl)-pyridinium-methansulfonate

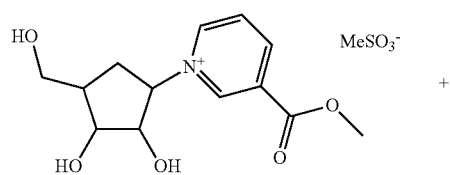

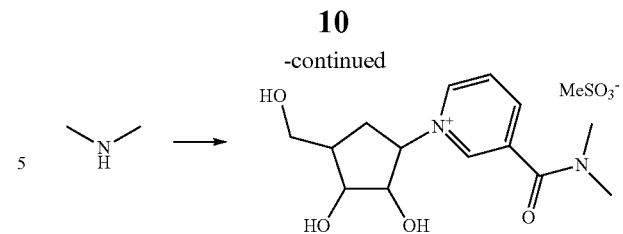

3-N,N-Dimethylcarbamoyl-1-(2,3-dihydroxy-4-hydroxymethyl-cyclopentyl)-pyridinium-methansulfonate was obtained similarly to 3-Carbamoyl-1-(2,3-dihydroxy-4-hydroxymethyl-cyclopentyl)-pyridinium-methansulfonate by reacting of the methylester from Example 3 with a solution of dimethylamine in THF.

Example 6

Coupling of a Vinamidinium Salt to a TAMRA Dye

By reacting a vinamidinium salt with a modified TAMRA dye an N-TAMRA-substituted nicotinic acid ester is formed.

The cyclization reaction is performed with an amino-modified TAMRA dye.

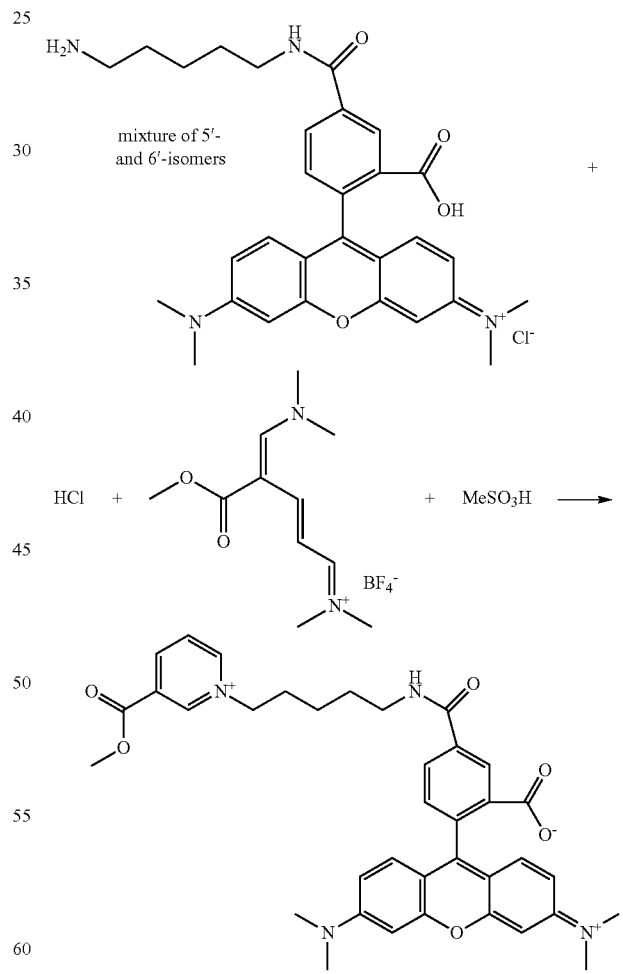

The amino-modified TAMRA dye (see above-mixture of 5- and 6 isomers) (19.8 mg, 35.93 μmol) was dissolved in methanolic HCl (0.125M, 201 μl, 25.15 μmol). The mixture was heated to 65° C. and a solution of vinamidinium salt (10.7 mg, 35.93 μmol) in MeSO3H (0.154M in MeOH/DMF (1:1), 233 µl, 35.93 µmol) was added slowly within 2.5 h at the same temperature. After the addition of the vinamidinium salt solution the reaction mixture was stirred for 16 h at room temperature. The solvent was removed under reduced pressure and purified by HPLC (Hypersil ODS) with an acetonitril/water gradient. The purified product was dissolved in methanolic HCl and evaporated under reduced pressure to give 16.6 mg (60%) of the TAMRA pyridinium conjugate.

MS: ESI: M+=636.98 (24).

All publications, patents and applications cited in this disclosure are incorporated herein by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for synthesis of an N-substituted pyridinium compound according to Formula III,

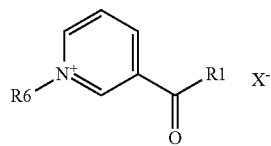

Formula III the method comprising the steps of:
a) providing a pentamethinium salt according to Formula I

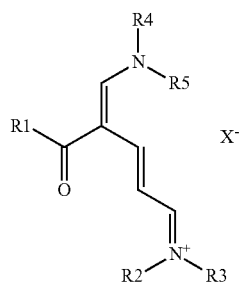

Formula I wherein X− is a counter ion;

R1 is alkoxy selected from O-methyl, O-ethyl, O-propyl, and O-isobutyl; and R2 to R5 independently are methyl or ethyl, b) reacting the pentamethinium salt of step (a) with a primary amine of Formula II,

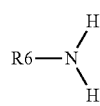

Formula II wherein R6 is

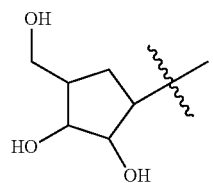

2. The method according to claim 1, further comprising recovering an N-substituted pyridinium according to Formula III.

3. The method according to claim 1, wherein X− is selected from dodecyl sulfate, chloride, tetrafluorophosphate, tetrafluoroborate and $ClO_4^-$.

4. The method of claim 1, wherein in step (b) both the primary amine and its corresponding protonated amine are present.

5. The method of claim 4, wherein the ratio of primary amine to its corresponding protonated amine is from 2:1 to 1:50.

6. The method of claim 4, wherein the ratio of primary amine to its corresponding protonated amine is from 1:1 to 1:20.

7. The method of claim 1, wherein R1 is $OCH_3$.

8. The method of claim 1, wherein R2 to R5 are methyl.

9. The method of claim 1, wherein the primary amine according to Formula II is (1R,2S,3R,4R)-2,3 dihydroxy-4-hydroxymethyl-1-aminocyclopentane.

10. The method of claim 9, wherein the pentamethinium salt according to Formula I is 5-dimethyl-amino-4-methoxy-carbonyl-penta-2,4-dimethyl-dienylidene ammoniumtetrafluoroborate, and X− is tetrafluoroborate.

* * * * *